(12) United States Patent
Eberle et al.

(10) Patent No.: US 6,823,210 B2
(45) Date of Patent: Nov. 23, 2004

(54) DATA MANAGEMENT SYSTEM FOR IMPLANTABLE CARDIAC DEVICE

(75) Inventors: Jason W. Eberle, St. Louis Park, MN (US); Hiten J. Doshi, Plymouth, MN (US); LeAnne Marie Mackey, St. Louis Park, MN (US); James O. Gilkerson, Stillwater, MN (US); Vickie L. Conley, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 47 days.

(21) Appl. No.: 10/397,460

(22) Filed: Mar. 26, 2003

(65) Prior Publication Data

US 2003/0187365 A1 Oct. 2, 2003

Related U.S. Application Data

(63) Continuation of application No. 10/369,095, filed on Feb. 17, 2003, now abandoned, which is a continuation of application No. 09/382,034, filed on Aug. 24, 1999, now Pat. No. 6,526,314, which is a continuation-in-part of application No. 09/378,317, filed on Aug. 20, 1999, now abandoned.

(51) Int. Cl.[7] .............................. A61B 5/00; A61B 5/04
(52) U.S. Cl. .......................... 600/523; 600/509; 607/9; 607/59
(58) Field of Search ................................. 600/523, 509, 600/300; 607/9, 59

(56) References Cited

U.S. PATENT DOCUMENTS

| | | | |
|---|---|---|---|
| 4,583,553 A | 4/1986 | Shah et al. | 128/704 |
| 4,945,477 A | 7/1990 | Edwards | 364/413.06 |
| 5,007,431 A | 4/1991 | Donehoo, III | 128/696 |
| 5,513,645 A | 5/1996 | Jacobson et al. | 128/710 |
| 5,640,496 A | 6/1997 | Hardy et al. | 395/121 |
| 5,673,031 A | 9/1997 | Meier | 340/825.08 |
| 5,732,708 A | 3/1998 | Nau et al. | 128/710 |
| 5,859,981 A | 1/1999 | Levin et al. | 395/200.68 |
| 5,908,392 A | 6/1999 | Wilson et al. | 600/509 |
| 5,940,771 A | 8/1999 | Gollnick et al. | 455/517 |
| 5,942,916 A | 8/1999 | Matsbara et al. | 326/83 |
| 6,009,472 A | 12/1999 | Boudou et al. | 709/232 |

FOREIGN PATENT DOCUMENTS

EP 0832600 9/1997 ............ A61B/5/00

*Primary Examiner*—Carl Layno
(74) *Attorney, Agent, or Firm*—Schwegman, Lundberg, Woessner & Kluth, P.A.

(57) ABSTRACT

A system and method for storing episodic data collected by an implantable medical device. If there are no unallocated storage locations, collected data associated with an episode is stored in locations that are freed from allocations to previous episodes. The least recently allocated of the storage locations allocated to episodes of a lower priority type may be freed first in order to maintain storage of higher priority episodic data. The method and system also allows a specified ratio of stored data allocated to episodes of one priority type to that of another priority type to be maintained.

30 Claims, 3 Drawing Sheets

| | | | | |
|---|---|---|---|---|
| 00 | NULL | 00 | 00 | ← VTR HIGH PRIORITY NODE |
| | | 00 | 00 | |
| 01 | NULL | 01 | 00 | ← VTR LOW PRIORITY NODE |
| | | 01 | 00 | |
| 02 | NULL | 02 | 00 | ← ATR NODE |
| | | 02 | 00 | |
| 03 | NULL | 03 | 00 | ← FREE NODE |
| | | 03 | 00 | |
| 04 | NULL | 00 | 04 | ← ALL NODE |
| | | 00 | 04 | |
| 05 | 0X3B | 00 | 00 | |
| | | 00 | 0C | |
| 06 | 0X1A | 0A | F9 | |
| | | 00 | 09 | ~10 |
| 07 | 0X0E | 00 | 0A | |
| | | 03 | 03 | |
| 08 | 0X03 | 03 | 07 | |
| | | 00 | 0B | |
| 09 | 0X02 | 04 | 04 | |
| | | 07 | 08 | |
| 0A | 0X15 | F9 | 09 | |
| | | 02 | 02 | |
| 0B | NULL | 00 | 00 | |
| | | 00 | 0D | |
| 0C | NULL | 00 | 00 | |
| | | 00 | 0E | |

FIG. 1A

| IDX | PTR | NEW | NEW ALL | ~102 |
|---|---|---|---|---|
| | | OLD | OLD ALL | ~103 |

DATA MANAGEMENT SYSTEM FOR IMPLANTABLE CARDIAC DEVICE

CROSS-REFERENCE TO RELATED APPLICATION(S)

This application is a continuation of U.S. patent application Ser. No. 10/369,095, filed on Feb. 17, 2003 now abandoned, which is a continuation of U.S. patent application Ser. No. 09/382,034, filed on Aug. 24, 1999, now issued as U.S. Pat. No. 6,526,314, which is a continuation-in-part of U.S. patent application Ser. No. 09/378,317, filed on Aug. 20, 1999, now abandoned, the specifications of which are incorporated by reference herein.

FIELD OF THE INVENTION

This invention pertains to implantable medical devices, such as cardiac pacemakers and implantable cardioverter/defibrillators, with data gathering capabilities. In particular, the invention relates to systems and methods for managing the storage and retrieval of episodic information gathered during operation of the device.

BACKGROUND

Implantable medical devices, such as cardiac pacemakers and implantable cardioverter/defibrillators have a limited amount of memory for storing data associated with episodes and therapy attempts. Previous methods of data storage have used a simple first-in, first-out rule for storing the data associated with episodes and therapy attempts with the assumption that there is enough memory so all data of interest can be retrieved before it is overwritten by newer data. Previous devices have also partitioned the data by type (electrogram data, interval data, episode and attempt data) where the first-in, first-out rule is applied individually to each type of data.

Although newer devices have increased the amount of memory available for storage, the assumption that data not yet retrieved still exists in device memory may still not hold true in many cases. For example, electrogram data almost always get overwritten first because a smaller amount of storage is available for electrogram data relative to the amounts dedicated to interval data and episode data. There are also cases where a patient has recurring arrhythmias of a certain type which overwrite the data from the infrequent arrhythmias which are of real interest to the physician. Newer devices are expanding the scope of arrhythmias that can be treated and consequently more data is generated for the newer types of arrhythmias. This leads to a need to manage the data storage such that the data of most interest is preserved.

SUMMARY OF THE INVENTION

The present invention is a system and method for storing episodic data collected by an implantable medical device. In one embodiment, previously used data storage locations are freed for overwriting with new data in accordance with a priority protection scheme. A data storage segmentation scheme may also be used that attempts to maintain a specified ratio of types stored data if unallocated storage space is unavailable.

In a particular implementation of the invention, collected data associated with an episode is stored in data storage locations referenced by storage nodes, where an episode is defined as any detected condition requiring the recordation of data. A linked list of unallocated storage nodes is maintained so that a storage node from the unallocated list can be allocated to each episode for which collected data is to be stored. In addition, a priority type linked list corresponding to each one of a plurality of episode priority types is also maintained, wherein each priority type linked list comprises storage nodes allocated to episodes of a particular type linked in an order that corresponds to when the episodes occurred. When the unallocated list of storage nodes is empty, storage nodes are freed for allocation to a present episode by freeing the oldest data storage node from one of the priority type lists, wherein the freed node is taken from a lower priority list in preference to a higher priority list. In accordance with a data storage segmentation scheme, storage nodes may be freed from priority type lists and allocated to new episodes in a manner that attempts to maintain the number of stored episodes of a particular type below a specified maximum number.

The storage nodes may reference a plurality of locations for storing a plurality of types of data associated with the episode. In a specific embodiment, data storage locations may be allocated to therapy attempts associated with an episode, and data collected prior to onset of the episode may be stored in a location referenced by the data storage node allocated to the episode. In a further specific embodiment, data collected before and after the therapy attempt may be stored in locations referenced by the data storage node allocated to the attempt.

BRIEF DESCRIPTION OF THE DRAWINGS

FIG. 1A is a representation of the history management structure.

FIG. 1B depicts the fields of a single node of the history management structure.

DETAILED DESCRIPTION OF THE INVENTION

Figures 2A, 2B:
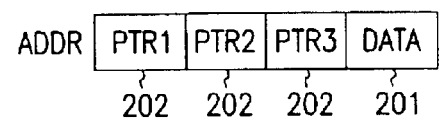
FIG. 2A is a representation of the history storage structure.
FIG. 2B depicts the fields of a history storage node.

As aforesaid, the present invention is a method and system for storing episodic data collected by an implantable medical device. An "episode" may be defined as any condition detected by the device via its sensing channels that requires the recordation of data. An episode may be, for example, a clinically significant condition occurring in a patient for which data recorded immediately prior to, during, and/or after the onset of the episode constitutes useful information for the treating clinician when the data is retrieved from the device with a programmer or similar telemetry device. Another type of episodic data is data collected before and after any therapy attempts performed by the device after detection of the onset of an episode requiring such therapy. For example, in an implantable cardioverter/defibrillator (ICD), a detected cardiac arrhythmia may constitute an episode, and any cardioversion/defibrillation shocks delivered to the heart in response to the arrhythmia would constitute therapy attempts associated with the episode. Similarly, in a pacemaker, a bradycardic or tachycardic arrhythmia could be an episode requiring the recordation of data, and any pacing therapy delivered in response would be a therapy attempt associated with the episode.

Data may be collected by an implantable medical device that incorporates the present invention via sensing channels that sense physiological variables. In a pacemaker/ICD device, sensing channels comprise electrodes and amplifiers for sensing cardiac electrical activity. The sensing channel signals may then be used to derive an electrogram, which is time referenced recording of cardiac electrical activity from the location of the electrode. (Electrograms are thus analogous to the familiar electrocardiogram or EKG which is obtained from external electrodes on the body surface.) Sensing channel signals may also be used to derive interval data which is a time referenced recording of the time intervals between cardiac events such as depolarizations and repolarizations occurring in the atria or ventricles. In certain devices, data may be continually stored in a circular input buffer as it is collected with the oldest data in the buffer being continually overwritten. Episodic data can be stored by transferring the data in the input buffer to a more permanent location after onset of an episode (or therapy attempt) and for a specified time thereafter. The continual storage of data before onset of the episode (or therapy attempt) also allows pre-episode (or pre-attempt) data to be stored and associated with the episode (or attempt).

In one specific embodiment, a data storage system in accordance with the invention comprises a number of interrelated data structures. A history storage structure comprising an array of nodes (wherein the terms "nodes" and "elements" are synonymous as used herein) used to reference data storage locations. In order to store data associated with an episode, a history storage node is allocated to the episode. The history storage node allocated to a new episode is taken from a linked list of unallocated history storage nodes if possible (i.e., if the list is not empty), else the node is allocated from a list of previously allocated history storage nodes. The system further includes a priority type linked list of previously allocated history storage nodes for each one of a plurality of types of episodes. Episodes are classified as being one of a plurality of priority types going from lower to higher, where a higher priority episode would be one regarded as more significant or of greater interest so it should be preferentially retained in storage. When a history storage node is allocated to an episode, the node is placed in a priority type linked list in accordance with the type of episode to which the node has been allocated. The history storage node may have a data field that indicates whether the node has been allocated to an episode or is free. The system may also include a priority protection scheme so that when a previously allocated node must be allocated to a new episode, the oldest node from one of the priority type lists is freed for allocation to the new episode, with the freed node taken from a lower priority list in preference to a higher priority list. A data storage segmentation scheme may be also be employed such that nodes are freed from priority type lists and allocated to new episodes in a manner such that a specified maximum number of stored episodes of one particular type will not be exceeded.

A further refinement in the system may be had by including a history management structure comprising an array of nodes, such that for each history storage node allocated to an episode, a history management node is also allocated to the episode and associated with the allocated history storage node. Each allocated history management node has a storage link field that points to the history storage node associated therewith. The priority type linked lists of history storage nodes may then be formed by linking associated history management nodes, where each allocated history management node has a link field pointing to an adjacent node in a priority type linked list of history management nodes. The priority type linked lists may be doubly linked lists with each allocated history management node having link fields pointing to adjacent nodes in both directions, which then allows insertions and deletions to be made at arbitrary points within the list without a list traversal. Another linked list that may be included is a doubly linked list of all allocated history management nodes, with each allocated node having link fields pointing to adjacent nodes in both directions in the all allocated node list. The nodes of the priority type linked lists and the all allocated linked list are linked sequentially in accordance with when the episodes to which the nodes are allocated occurred. Both the all allocated list and the priority type lists thus constitute a sequence of episodes for which data has been collected in the order in which the episodes occurred.

The system may further include a data storage structure comprising an array of nodes, where for each history storage and history management node allocated to an episode, a data storage node is also allocated to the episode and associated with the allocated history storage and history management node. Each allocated history storage node has a link field pointing to an associated data storage node, and each data storage node references a data storage block in which episodic data is actually stored. Episodic data may be stored in a plurality of data storage blocks referenced by a linked list of data storage nodes allocated to the episode with each allocated data storage node having a link field for pointing to an adjacent data storage node in the linked list.

The history management structure may be further modified to include nodes designated as list heads for the unallocated linked list, the all allocated linked list, and the priority type linked lists. In order to facilitate additions and deletions to all the lists, they may be made doubly linked with each history management node designated as a list head having link fields for pointing to adjacent nodes in both directions. (A "list head" is a special identifiable node in a circularly linked list.)

The system may also allow for the recordation of data related to therapy attempts delivered by the device. Episodic data collected before and after a therapy attempt associated with an episode may be stored in a plurality of data storage blocks referenced by a linked list of data storage nodes allocated to storing data collected before and after the attempt. In order to link attempt data to the episode with which the data is associated, a history storage node allocated to an episode has a link field that may reference a history storage node allocated to a therapy attempt associated with the episode. A history storage node allocated to an attempt has a data field in which is stored a value indicating that the node is allocated to an attempt, a link field that references a data storage node allocated to storing data collected before the therapy attempt, and a link field that references a data storage node allocated to storing data collected after the therapy attempt. The history storage node allocated to an attempt further has a link field that may reference history storage nodes allocated to any subsequent attempts.

A history storage node may be allocated to a new therapy attempt associated with an episode from the list of unallocated history storage nodes unless the unallocated list is empty, in which case the oldest node from one of the priority type lists is freed and added to the unallocated list for allocation to the new episode. The freed node is taken from a lower priority list in preference to a higher priority list in order to provide priority protection. In order to provide data storage segmentation, nodes are freed from priority type lists and allocated to new episodes in a manner such that a specified maximum number of stored episodes of one particular type will not be exceeded. Priority protection and data storage segmentation may also be combined. Data storage nodes (and the data storage blocks to which they refer) may be allocated in a similar manner.

As described above, the system allocates history storage nodes and history management nodes by freeing the nodes from one of the priority lists when the unallocated list is empty. When a history storage node allocated to an episode is freed, the history management node allocated to the episode, all history storage nodes allocated to therapy attempts associated with the episode, and all data storage nodes and blocks allocated to the episode or associated attempts are also freed.

The following description is of a particular embodiment of the invention as implemented in an implantable cardiac device having the capability of collecting data by sensing cardiac intervals and electrograms, and further having the capability of delivering electrical therapy to the heart. The data storage system to be described is implemented in software in a microprocessor-based device and stores data associated with specific detected episodes. Episodes may be defined as a defined set of collected data that corresponds to a type of cardiac arrhythmia that either requires delivery of electrical therapy or is clinically significant enough to require recording of the data.

The system uses a priority protection scheme that preserves episode data with certain types of arrhythmias. Episodes are classified high or low priority based on predefined criteria. High priority episodes are only overwritten if all space available for storing data is occupied by previous high priority episodes. The system also employs a data storage segmentation scheme that allows storage of both atrial tachyarrhythmia response (ATR) and ventricular tachyarrhythmia response (VTR) episode detail, interval data, and electrogram data in memory, while restricting the amount of space given to each type within a programmable limit. The storage segmentation can be reprogrammed at any time without losing any stored data. When the storage segmentation is changed, new episode data of one type will overwrite episode data of the other type until the proper data storage segmentation is once again established.

Three types of history data are maintained: episode and attempt data, interval data, and electrogram data. Episode and attempt data are maintained in the history storage structure. Interval data is maintained in the interval data storage structure, and electrogram data is maintained in the electrogram data storage structure. A fourth structure, the history management structure 10 is shown in FIG. 1A, and is used to track the chronological order of the episodes. This structure tracks the order of all episodes stored in memory, as well as the order of the individual classifications of episodes (ATR, VTR high priority, and VTR low priority). The history management structure is the starting point for accessing history data.

The history management structure is a constant sized array of elements or nodes used to keep track of all episodes stored in memory. Each element 100 is itself a data structure containing five indices as shown in FIG. 2B:

1) the history storage location index 101, which is an index into the history storage structure described below and points to the history storage node allocated to the episode;

2) the newer episode index 102 in the list of all episodes (i.e., the all allocated list of nodes);

3) the older episode index 103 in the list of all episodes;

4) the newer episode index 104 in the list of all episodes of the same classification (i.e., the priority type list to which the node has been assigned); and, 5) the older episode index 105 in the list of all episodes of the same classification.

(The terms index, pointer, link, or reference as used herein denotes a mechanism for accessing a specific memory location.)

Episodes and attempts are stored in the history storage structure 20 represented in FIG. 2A. Each node 200 of the history storage structure is made up of two components, the data field 201 and the link fields 202. FIG. 2B depicts the components of a history storage node. The data component 201 of the history storage element identifies how the element is allocated and can either contain episode data, attempt data, or no data if the node is free. If the data is episode data, it can be a ventricular tachyarrhythmia response episode or an atrial tachyarrhythmia response episode. The link fields 202 of the node vary according to whether the node is allocated to an episode, an attempt or is free as indicated by the type of data currently in the data field 201. If the data field of the node contains episode data, the link fields contain the index of the first attempt node in the episode (i.e., the first history storage node allocated to a therapy attempt associated with the episode), the index of the first segment of interval data for the episode, and the index of the first segment of electrogram data for the onset electrogram strip. If the data field of the node contains attempt data, the link fields contain the index of the next attempt node in the episode, the index of the first segment of pre-attempt electrogram data for the attempt, and the index of the first segment of post-attempt electrogram data for the attempt. If the history storage node is free, the link field contains the index of the next free history storage node in a linked list of all free history storage nodes.

Interval data is segmented into constant sized data storage blocks. Multiple blocks are linked together to store the interval data for a single episode. These blocks are referenced by an index that identifies the location of the data storage block in memory and also identifies a corresponding node of an interval data storage structure. The sequence of the stored interval data is maintained within the data storage structure as a linked list of data storage nodes, where each node of the data storage structure has a link field that points to the corresponding data storage node of the next interval data storage block in the storage sequence.

Electrogram data is also segmented into constant sized data storage blocks. Multiple blocks are linked together to store the electrogram data for a single electrogram strip. These blocks are referenced by an index that identifies the location of the data storage block in memory and also identifies a corresponding node of an electrogram data storage structure. The sequence of the stored electrogram data is maintained within the data storage structure as a linked list of data storage nodes, where each node of the data storage structure has a link field that points to the corresponding data storage node of the next electrogram data storage block in the storage sequence.

At initialization, the history management nodes are placed in a doubly linked list. There are five reserved nodes in the history management structure that serve as list heads for five doubly linked lists of history management nodes. The first node is the unallocated list head which is used to access a linked list of those history management nodes that are not currently being used to track episode data. Initially, all nodes in the structure are linked to the unallocated list head. The second reserved node is the all allocated list head. The all allocated list head maintains the linked list of all episodes currently stored in memory, in the order in which they occurred. The other three reserved nodes are list heads used to track ATR episodes, VTR high priority episodes, and VTR low priority episodes. Each of these individual linked lists contains the episodes of that classification in the order which they occurred. Every stored episode is accounted for in one of these three lists, and in the all allocated list.

The unallocated history storage nodes are initially placed in a singly linked list, with the first free node pointed to by a storage node free pointer. Similarly, the unallocated interval data storage nodes are placed in a singly linked list pointed to by the interval data storage free pointer, and the electrogram data storage nodes are placed in a singly linked list pointed to by the electrogram data storage free pointer.

When an episode occurs, a new history storage node must be allocated. If there is a history storage node in the unallocated list, that node is used for the new episode. In a similar fashion, a history management node is taken from the unallocated list as pointed to by the unallocated list head node. The system is designed such that the number of history storage nodes in use is always greater than or equal to the number of history management nodes in use. This is because the history storage structure contains nodes allocated to both episodes and attempts, while the history management structure contains only nodes allocated to episodes. Any therapy attempts recorded during a VTR episode also requires the use of a history storage node. A free history storage node for an attempt is obtained using the same logic as was used to obtain a history storage node for the episode.

Figure 3:
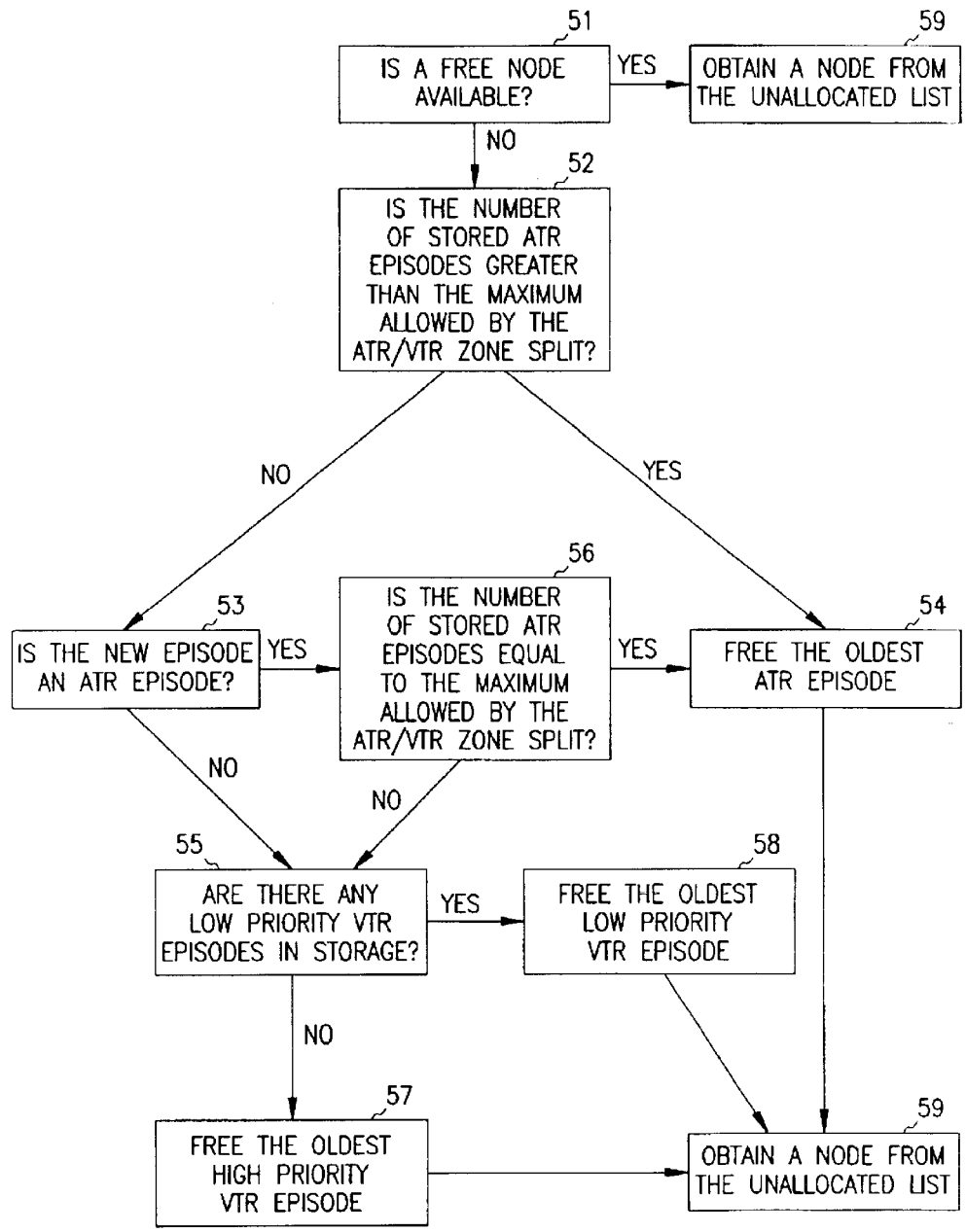
FIG. 3 is a flow chart of a particular decision-making process for freeing previously allocated storage locations.

FIG. 3 shows the decision-making process used to determine which history storage node is used for a new episode. At step 51, the unallocated list is checked and if a node is available, it is allocated to the episode at step 59. If no unallocated node exists, step 52 determines whether the number of ATR episodes is greater than the maximum allowed by the specified ATR/VTR zone split (i.e., the specified maximum number of stored ATR episodes and stored VTR episodes in accordance with the data segmentation scheme). If the specified zone split is already exceeded, it means that there are more stored ATR episodes than are allowed by the specified ATR/VTR zone split, which can happen if the specified split is changed or if the number of ATR episodes crosses the ATR/VTR split boundary before the unallocated list is empty. In that case, the node allocated to the oldest ATR episode is freed at step 54 and allocated to the new episode at step 59. The index of the oldest ATR episode is found in the ATR list head of the history management structure.

If the ATR/VTR zone split is at the specified value or there are more VTR episodes stored than are allowed by the specified zone split, it is next determined whether the new episode is an ATR episode at step 53. If the answer is yes, step 56 determines if the number of stored ATR episodes is equal to the specified allowable maximum (which means that the mix of stored episodes complies with the specified zone split), and if so the oldest ATR episode is replaced with the new ATR episode at steps 54 and 59. If the answer at step 56 is no, there are more VTR episodes in memory than are allowed by the specified zone split, and a VTR episode must be freed. A VTR episode is also freed if it is determined at step 53 that the new episode is a VTR episode.

Before freeing a VTR episode, step 55 determines whether there are any low priority VTR episodes in storage. If so, the oldest VTR episode is freed at step 58, with the index of the oldest low priority VTR episode being found in the low priority VTR list head of the history management structure. Step 59, as before, then allocates the newly freed node to new episode. If there are no low priority VTR episodes in storage, the oldest high priority VTR episode is freed at step 57, with the index of the oldest high priority episode being found in the high priority VTR list head of the history management structure, and allocated to the new episode at step 59.

When an episode history storage node is freed, the associated history management structure node allocated to the same episode is also freed, as well as all attempt history storage nodes, interval data storage blocks, and electrogram data storage blocks associated with that episode. If an attempt history storage node is freed, all electrogram data storage blocks associated with the attempt are also freed.

Obtaining free interval data storage blocks and electrogram data storage blocks employs the same logic as obtaining free history storage nodes. When an interval data storage block is freed, all interval data storage blocks associated with an episode are freed. When an electrogram data storage block is freed, all electrogram data storage blocks associated with an electrogram strip are freed.

Once episode data has been retrieved from the device, it is no longer necessary to have the data protected. Therefore, the system preferably provides a method of unprotecting data on command from a telemetry device so that all high priority VTR episodes can be placed in the low priority VTR episode list. The chronological order of the episodes is maintained when the data is moved.

What is claimed is:

1. A data storage system, comprising:

history storage nodes each adapted to be allocated to an episode for referencing a location where data related to the episode is stored, the data collected by an implantable medical device;

a linked list of unallocated history storage nodes; and a plurality of priority type linked lists of allocated history storage nodes, including:

at least one atrial linked list of history storage nodes allocated to atrial tachyarrhythmia response (ATR) episodes; and at least one ventricular linked list of history storage nodes allocated to ventricular tachyarrhythmia response (VTR) episodes, wherein:

a history storage node from the linked list of unallocated history storage nodes is allocated to a new episode if the linked list of unallocated history storage nodes is not empty; and a history storage node from one of the priority type linked lists of allocated history storage nodes is selected, based on a predetermined relative priority of each of the priority type linked lists of allocated history storage nodes, for being allocated to the new episode if the linked list of unallocated history storage nodes is empty.

2. The system of claim 1, wherein the priority type linked lists of allocated history storage nodes comprise:

the at least one atrial linked list of history storage nodes allocated to ATR episodes;

a high priority ventricular linked list of history storage nodes allocated to VTR high priority episodes; and a low priority ventricular linked list of history storage nodes allocated to VTR low priority episodes.

3. The system of claim 1, wherein the priority type linked lists of allocated history storage nodes are each programmed to allow a maximum number of the history storage nodes.

4. The system of claim 1, further comprising history management nodes adapted to track a chronological order of stored episodes, the history management nodes each adapted to be allocated to an episode associated with one of the allocated history storage nodes and associated with that allocated history storage node.

5. The system of claim 4, further comprising priority type linked lists of history management nodes including:
   at least one atrial linked list of history management nodes allocated to ATR episodes; and
   at least one ventricular linked list of history management nodes allocated to ventricular VTR episodes.

6. The system of claim 5, wherein the priority type linked lists of history management nodes comprise:
   the at least one atrial linked list of history management nodes allocated to ATR episodes;
   a high priority ventricular linked list of history management nodes allocated to VTR high priority episodes; and
   a low priority ventricular linked list of history management storage nodes allocated to VTR low priority episodes.

7. The system of claim 5, wherein the history management nodes each have a storage link field pointing to the associated allocated history storage node, to allow formation of the priority type linked lists of allocated history storage nodes by linking associated history management nodes with each allocated history management node having a link field pointing to an adjacent node in one of the priority type linked lists of history management nodes.

8. The system of claim 7, wherein the priority type linked lists of history management nodes are doubly linked lists with each allocated history management node having link fields pointing to adjacent nodes in both directions.

9. The system of claim 8, further comprising an all allocated linked list of history management nodes being a doubly linked list of all allocated history management nodes with each allocated history management node having link fields pointing to adjacent nodes in both directions in the all allocated node list.

10. The system of claim 9, further comprising:
    data storage nodes each adapted to be allocated to an episode to which one of the allocated history storage nodes and one of the history management nodes are allocated, the history storage nodes each having a link field pointing to an associated data storage node; and
    a plurality of data storage blocks to store episodic data, wherein the data storage nodes each reference one of the plurality of data storage blocks.

11. The system of claim 10, further comprising a linked list of allocated data storage nodes, wherein each of the allocated data storage nodes has a link field for pointing to an adjacent node in the linked list of allocated data storage nodes.

12. A method for storing data collected by an implantable medical device, the method comprising:
    receiving episodes recorded by the implantable medical device, the episodes each including data related to a cardiac arrhythmia;
    referencing locations for storing the episodes with history storage nodes each adapted to be allocated to one of the episodes;
    maintaining a linked list of unallocated history storage nodes;
    maintaining priority type linked lists of allocated history storage nodes including:
    at least one atrial linked list of history storage nodes allocated to atrial tachyarrhythmia response (ATR) episodes; and
    at least one ventricular linked list of history storage nodes allocated to ventricular tachyarrhythmia response (VTR) episodes;
    selecting one history storage node from the linked list of unallocated history storage nodes if the linked list of unallocated history storage nodes is not empty;
    selecting one history storage node from one of the priority type linked lists of allocated history storage nodes, based on a predetermined relative priority of each of the priority type linked lists of allocated history storage nodes, if the linked list of unallocated history storage nodes is empty; and
    allocating the selected history storage node to a new episode.

13. The method of claim 12, wherein receiving episodes comprises receiving collected data sets each corresponding to a type of cardiac arrhythmia that requires delivery of an electrical therapy.

14. The method of claim 13, wherein receiving episodes comprises receiving data sets each related to a therapy attempt associated with one of the episodes.

15. The method of claim 12, wherein maintaining the priority type linked lists of allocated history storage nodes comprises maintaining:
    the at least one atrial linked list of history storage nodes allocated to ATR episodes;
    a high priority ventricular linked list of history storage nodes allocated to VTR high priority episodes; and
    a low priority ventricular linked list of history storage nodes allocated to VTR low priority episodes.

16. The method of claim 12, further comprising limiting the number of the allocated historical storage nodes in each of the priority type linked lists of allocated history storage nodes to a predetermined maximum number.

17. The method of claim 12, further comprising:
    maintaining an array of history management nodes to track a chronological order of stored episodes; and
    allocating each of the history management nodes to an episode associated with one of the allocated history storage nodes and associated with that allocated history storage node.

18. The method of claim 17, further comprising maintaining priority type linked lists of history management nodes including:
    at least one atrial linked list of history management nodes allocated to ATR episodes; and
    at least one ventricular linked list of history management nodes allocated to ventricular VTR episodes.

19. The method of claim 18, wherein maintaining the priority type linked lists of history management nodes comprises maintaining:
    the at least one atrial linked list of history management nodes allocated to ATR episodes;
    a high priority ventricular linked list of history management nodes allocated to VTR high priority episodes; and
    a low priority ventricular linked list of history management storage nodes allocated to VTR low priority episodes.

20. The method of claim 18, further comprising forming priority type linked lists of allocated history storage nodes by linking the associated history management nodes with each allocated history management node having a link field pointing to an adjacent node in one of the priority type linked list of history management nodes, wherein the allocated history management nodes each have a storage link field pointing to the associated history storage node.

21. The method of claim 20, wherein maintaining the priority type linked lists of history management nodes comprises maintaining doubly linked lists with each allocated history management node having link fields pointing to adjacent nodes in both directions.

22. The method of claim 21, further comprising maintaining a doubly linked list of all allocated history management nodes with each allocated history management node having link fields pointing to adjacent nodes in both directions in the linked list of all allocated history management nodes.

23. The method of claim 22, further comprising:

maintaining an array of data storage nodes each adapted to be allocated to an episode to which one of the allocated history storage nodes and one of the history management nodes are allocated, the history storage nodes each having a link field pointing to an associated data storage node; and maintaining a plurality of data storage blocks to store episodic data, wherein the data storage nodes each reference one of the plurality of data storage blocks.

24. The method of claim 23, further comprising maintaining a linked list of allocated data storage nodes each having a link field for pointing to an adjacent node in the linked list of allocated data storage nodes.

25. A data storage system for storing data collected by an implantable medical device, the system comprising:

data storage nodes each adapted to be allocated to an episode for referencing a location where data related to the episode is stored;

means for maintaining a linked list of unallocated data storage nodes;

means for allocating a data storage node from the unallocated list to a present episode;

means for maintaining priority type linked lists each corresponding to one type of a plurality of episode priority types, the priority type linked lists each including data storage nodes allocated to episodes of a particular type, the allocated data storage nodes linked in an order that corresponds to when the episodes occurred; and means for freeing the allocated data storage nodes for allocation to the present episode when the linked list of unallocated data storage nodes is empty by freeing the oldest data storage node from one of the priority type lists.

26. The system of claim 25, wherein the means for freeing the allocated data storage nodes comprises means for freeing data storage nodes from the priority type lists according to a predetermined priority unless a specified maximum number of stored episodes of one particular type would then be exceeded.

27. The system of claim 26, wherein the means for freeing the allocated data storage nodes comprises means for freeing one of the allocated data storage nodes from a lower priority list in preference to a higher priority list.

28. The system of claim 27, further comprising means for allocating a data storage node to a therapy attempt associated with an episode.

29. The system of claim 28, further comprising means for storing data collected prior to onset of the episode in a location referenced by the data storage node allocated to the episode.

30. The system of claim 29, further comprising means for storing data collected before and after the therapy attempt in locations referenced by the data storage node allocated to the attempt.

* * * * *